United States Patent
Itoh et al.

(10) Patent No.: US 10,927,049 B2
(45) Date of Patent: Feb. 23, 2021

(54) METHOD OF PRODUCING HYDROCARBON AND APPARATUS FOR PRODUCING HYDROCARBON

(71) Applicant: CANON KABUSHIKI KAISHA, Tokyo (JP)

(72) Inventors: Miki Itoh, Yokohama (JP); Hironao Sajiki, Gifu (JP); Yoshinari Sawama, Gifu (JP); Miki Niikawa, Gifu (JP); Kwihwan Park, Gifu (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 16/653,718

(22) Filed: Oct. 15, 2019

(65) Prior Publication Data

US 2020/0123079 A1 Apr. 23, 2020

(30) Foreign Application Priority Data

Oct. 19, 2018 (JP) .............................. JP2018-197182

(51) Int. Cl.
*C07C 1/12* (2006.01)
*B01J 10/00* (2006.01)
(Continued)

(52) U.S. Cl.
CPC ................. *C07C 1/12* (2013.01); *B01J 10/00* (2013.01); *B01J 19/0006* (2013.01); *B01J 19/18* (2013.01); *B01J 19/285* (2013.01); *C07C 9/04* (2013.01); *B01J 2219/00162* (2013.01); *B01J 2219/00957* (2013.01); *B01J 2219/0286* (2013.01); *B01J 2219/30408* (2013.01)

(58) Field of Classification Search
CPC . B01J 10/00; B01J 19/285; B01J 8/008; B01J 8/10; B01J 8/16; B01J 2219/00162; B01J 2219/00957; B01J 2219/0286; B01J 2219/30408; C07C 1/12
See application file for complete search history.

(56) References Cited

U.S. PATENT DOCUMENTS 2,465,462 A * 3/1949 Layng .................. C07C 1/0485
518/703
2,635,949 A * 4/1953 Fenske ...................... B01J 8/10
422/140

FOREIGN PATENT DOCUMENTS

| JP | 2004-202418 A | 7/2004 |
| JP | 2007-031169 A | 2/2007 |
| JP | 2013-176773 A | 9/2013 |

* cited by examiner

*Primary Examiner* — Lessanework Seifu
(74) *Attorney, Agent, or Firm* — Canon U.S.A., Inc., IP Division

(57) ABSTRACT

A hydrocarbon is produced by applying mechanical energy to a metal body containing stainless steel by solid-solid contact so that a contact pressure per unit area is 30 kPa or more, in the presence of a gas containing carbon dioxide and a hydrogen source, thereby adding hydrogen to carbon dioxide. Further, a hydrocarbon is produced by providing a reaction vessel for applying mechanical energy to a metal body by solid-solid contact in the presence of a gas containing carbon dioxide and a hydrogen source, a gas introduction unit for introducing the gas containing carbon dioxide to the reaction vessel, a hydrogen source introduction unit for introducing the hydrogen source to the reaction vessel, and a gas discharge unit for discharging a gas containing the hydrocarbon produced in the reaction vessel, and adding hydrogen to the carbon dioxide in the reaction vessel.

23 Claims, 10 Drawing Sheets

(51) Int. Cl.
*B01J 19/28* (2006.01)
*C07C 9/04* (2006.01)
*B01J 19/00* (2006.01)
*B01J 19/18* (2006.01)

METHOD OF PRODUCING HYDROCARBON AND APPARATUS FOR PRODUCING HYDROCARBON

BACKGROUND OF THE INVENTION

Field of the Invention

The present disclosure relates to a method of producing a hydrocarbon and an apparatus for producing a hydrocarbon, and more particularly, to a method of producing a hydrocarbon and an apparatus for producing a hydrocarbon from carbon dioxide which is one of the greenhouse gases.

Description of the Related Art

Currently, efforts to reduce an emission amount of carbon dioxide which is one of the greenhouse gases are in progress worldwide. Further, as a countermeasure for released carbon dioxide, development of a technology for storing separated and recovered carbon dioxide in the ground (CCS: carbon dioxide capture and storage) is also in progress. Also, as an effort to further improve environmental effectiveness and recycling, expectations for a technology to make valuable materials such as petroleum alternative fuels and chemical raw materials from recovered carbon dioxide (CCU: carbon dioxide capture and utilization), have been increased.

Representatives of technologies actively undertaken as CCU include biofuel derived from algae and artificial photosynthesis. Algae-derived biofuel is a fuel produced by culturing algae with sunlight and carbon dioxide and extracting oil from the concentrated and dried algae. Artificial photosynthesis is a technology to make hydrocarbons from carbon dioxide and water using light energy. Both technologies can recycle carbon dioxide and are environmentally effective, but have disadvantages in that a vast culture plant and a solar panel are required and efficiency is low. In addition, both rely only on sunlight as the energy source, and have restrictions in terms of the weather and installation location. Under such a background, a new technology for producing valuable materials from carbon dioxide is required.

As a conversion method of carbon dioxide which does not rely only on sunlight as an energy source, for example, Japanese Patent Application Laid-Open No. 2007-31169 is known. Japanese Patent Application Laid-Open No. 2007-31169 discloses a method in which a mechanical impact or stress is applied to a metal body or a material body containing a low-valent metal to activate a metal, and water is contacted and reacted with the metal to generate hydrogen. Then, at that time, carbon dioxide is introduced with water and interposed, thereby carbon oxide is converted to a carbonate and fixed.

Further, Japanese Patent Application Laid-Open No. 2004-202418 discloses an apparatus and a method of decomposing carbon dioxide by intermittently supplying high-pressure gas to a reaction chamber to generate shock waves, and impact-compressing a mixture of carbon dioxide-containing gas, a reactant material, and water vapor and heating the compressed mixture to a high temperature. Further, Japanese Patent Application Laid-Open No. 2013-176773 discloses a method of producing hydrogen or deuterium, characterized by a mechanochemical reaction in a planetary ball mill.

However, in Japanese Patent Application Laid-Open No. 2007-31169, carbon dioxide is fixed as a metal carbonate, and valuable materials such as petroleum alternative fuels and chemical raw materials are not produced.

In Japanese Patent Application Laid-Open No. 2004-202418, the type of materials produced after carbon dioxide decomposition is different depending on the type of reactant materials, but as in Japanese Patent Application Laid-Open No. 2007-31169, the material is not a valuable material but carbon monoxide or carbon itself. In particular, carbon monoxide is a toxic material and has a disadvantage that subsequent handling thereof is difficult.

SUMMARY OF THE INVENTION

The present disclosure has been made in view of the above disadvantages, and an aspect of the present disclosure is to provide a method of producing a hydrocarbon and an apparatus for producing a hydrocarbon, which can be driven by an energy source other than sunlight, and produce a hydrocarbon from carbon dioxide with high efficiency.

A method of producing a hydrocarbon from carbon dioxide according to the present disclosure includes: applying mechanical energy to a metal body containing stainless steel by solid-solid contact so that a contact pressure per unit area is 30 kPa or more, in the presence of a gas containing carbon dioxide and a hydrogen source, thereby adding hydrogen to carbon dioxide to produce a hydrocarbon.

Further, an apparatus for producing a hydrocarbon from carbon dioxide according to the present disclosure includes: a reaction vessel for applying mechanical energy to a metal body by solid-solid contact in the presence of a gas containing carbon dioxide and a hydrogen source, a gas introduction unit for introducing the gas containing carbon dioxide to the reaction vessel, a hydrogen source introduction unit for introducing the hydrogen source to the reaction vessel, and a gas discharge unit for discharging a gas containing a hydrocarbon produced in the reaction vessel, in which in the reaction vessel, hydrogen is added to carbon dioxide to produce a hydrocarbon.

The present disclosure can produce a hydrocarbon from carbon dioxide with high efficiency using an energy source other than sunlight.

Further features of the present disclosure will become apparent from the following description of exemplary embodiments with reference to the attached drawings.

DESCRIPTION OF THE EMBODIMENTS

Figure 1:
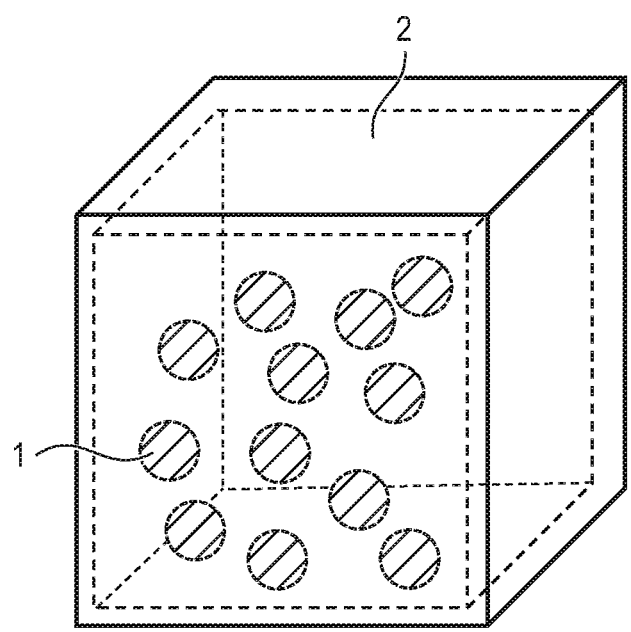
FIG. 1 is an example of a configuration in which a metal body and a hard body are brought into a point contact, according to the present disclosure.

Next, preferred embodiments of the present disclosure will be described in detail.

First Embodiment (Method of Producing Hydrocarbon)

First, a method of producing s hydrocarbon according to a first embodiment of the present disclosure will be described in detail.

A method of producing a hydrocarbon from carbon dioxide according to the present disclosure includes: applying mechanical energy to a metal body containing stainless steel by solid-solid contact so that a contact pressure per unit area is 30 kPa or more, in the presence of a gas containing carbon dioxide and a hydrogen source, thereby adding hydrogen to carbon dioxide to produce hydrocarbon.

The solid-solid contact is contact between a metal body and a hard body.

The gas containing carbon dioxide may be a gas having a ratio of carbon dioxide of 100%, or a mixed gas with other components. However, in order to increase production efficiency of a hydrocarbon, it is preferred that the ratio of carbon dioxide is high.

The hydrogen source is a material having hydrogen in the composition, and is a material which is a hydrogen supply source when hydrogen is added to carbon dioxide to produce a hydrocarbon. Hydrogen sources is reduced by the metal body and hydrogen is extracted. It is preferred that the hydrogen source is water, in view of the reactivity and availability thereof.

The hard body plays a role of applying mechanical energy to a system by contact with the metal body.

A metal body contains metal. A main role of metal is to extract hydrogen by reducing the hydrogen source, and to promote conversion of carbon dioxide into hydrocarbons by metal carbonation of carbon dioxide and hydrogenation of the metal carbonate.

There may be a reaction path in which decomposition and conversion of carbon dioxide proceed through direct hydrogenation of carbon, carbonation of the metal, and the like, but production efficiency of a hydrocarbon is increased by assigning the role mainly to the metal. Therefore, as the metal, it is preferred to use a metal having a valence which can be oxidized by the hydrogen source and also a valence which can be carbonated, that is, a low-valent metal in which it is possible to change a low valance to a high valance, and desirably a zero-valent metal.

In addition, besides a metal simple substance, an alloy is preferred from a viewpoint of reaction efficiency, and stainless steel is more preferred.

In the present disclosure, mechanical energy is applied to the metal body by solid-solid contact between hard body and the metal body.

Therefore, any shape and any material of the hard body can be used as long as mechanical energy can be applied to a surface of the metal body.

Further, it is preferred that a surface area of the metal body to which mechanical energy is applied, that is, a contact area with the hard body is large. In terms of reaction efficiency, a particulate or powdered metal body may be used. Furthermore, a surface of other materials may be coated with the metal body, which is a preferred form for reducing a weight of the metal body.

In addition, the shape, material, size, and the like of the hard body may be the same or different from the shape, material, size, and the like of the metal body. That is, the hard body and the metal body may be the same. In order to apply sufficient mechanical energy to the metal body, it is preferred that the hard body has any one of the size, weight, and hardness equal to or higher than that of the metal body. Even in the case that the hard body does not have one of those characteristics, mechanical energy can be efficiently applied by applying pressure or the like to the metal body through the hard body.

Further, the hard body may have a uniform composition, or may be a composite, for example, other materials coated with a material of the hard body.

Furthermore, it is preferred that the hard body itself is also the metal body, from viewpoints of reducing an energy loss and increasing a contact area of the metal body which receives mechanical energy. In this case, there is no limitation on the shape of the metal body such as ball, column, and plate shapes, as long as sufficient mechanical energy can be obtained by the contact between the metal bodies. Further, in order to increase the contact area as described above, a surface contact between plate shapes is also preferred.

In production of hydrocarbon according to the present disclosure, it is preferred that the following three reactions efficiently proceed as described above, and these proceed by adding mechanical energy to a reaction field.

(1) Extraction of hydrogen by a metal reducing a hydrogen source (2) Metal carbonation of carbon dioxide (3) Conversion to hydrocarbons by hydrogenation to metal carbonate Further, all three reactions involve the metal body. Therefore, it is essential to apply mechanical energy to the metal body.

In addition, (1) requires a hydrogen source, (2) requires carbon dioxide, and (3) requires hydrogen for each reactions, and in the presence thereof, it is necessary to add mechanical energy to the metal body.

The mechanical energy is applied by applying an impact force, stress, a frictional force, and the like to a surface of the metal body by solid-solid contact with the hard body, that is, contact of the hard body with the metal body. Therefore, it is possible to control an amount of the mechanical energy by controlling the impact force, stress, fractional force, and the like.

These forces directly contribute to progress of a decomposition reaction of carbon dioxide and the hydrogen source, and it is possible to change a consumption rate of carbon dioxide and a decomposition rate of carbon dioxide. Therefore, it is possible to prevent an excessive amount of the mechanical energy input for the reaction, by controlling the amount of the mechanical energy. Thus, a production amount of hydrocarbon relative to an input energy amount, that is, energy efficiency can be increased. For that reason, it is preferred to control the production amount or production efficiency of a hydrocarbon by controlling mechanical energy.

As a result of the control, the produced hydrocarbon includes carbon derived from carbon dioxide and hydrogen derived from the hydrogen source, and in particular, is hydrocarbons such as methane, ethane, and propane.

In addition, in the present disclosure, a carbon dioxide consumption rate is defined as a ratio of a value obtained by subtracting a remaining carbon dioxide amount from a charged carbon dioxide amount, relative to the charged carbon dioxide amount. Further, a carbon dioxide decomposition rate is defined as a ratio of a produced amount of hydrocarbons, in particular, a methane amount, relative to a charged carbon dioxide amount.

Further, it is preferred to detect and feed back an amount or concentration of remaining carbon dioxide and the produced hydrocarbon to control one or more of the amount of the gas containing carbon dioxide and the amount of the mechanical energy.

As described above, mechanical energy contributes to progress of the decomposition reaction of carbon dioxide and the hydrogen source, and changes the carbon dioxide consumption rate and the carbon dioxide decomposition rate.

For example, in the case that the hard body and the metal body are abraded to cause a change in a contact state, production ability of the surface of the metal body is lowered, or the like, there is a possibility that the mechanical energy is insufficient and the carbon dioxide consumption rate and the carbon dioxide decomposition rate are lowered. On the contrary, even in the case that the carbon dioxide consumption rate and the carbon dioxide decomposition rate are sufficient, when excessive mechanical energy is input, there is a possibility that energy efficiency is lowered.

When an amount or concentration of carbon dioxide or the produced hydrocarbon is detected and the detection results are fed back to control one or more of an introduction amount of the gas containing carbon dioxide and the amount of the mechanical energy, reaction efficiency and energy efficiency can be maintained to be high.

When production efficiency (carbon dioxide consumption rate and carbon dioxide decomposition rate) is low, it is preferred to increase the mechanical energy, and when production efficiency is high but a production amount is small, it is preferred to increase an introduction amount of gas. Further, when both the production amount and the production efficiency are sufficiently higher than those to be desired, the mechanical energy may be decreased and energy efficiency may be increased.

Further, in order to continue the reaction, undecomposed carbon dioxide and a hydrogen source should be brought into contact with the metal body. That is, mechanical energy is applied to the metal body as contact and non-contact between the hard body and the metal body are repeated, and new carbon dioxide and hydrogen source need to be brought into contact with the metal body during the non-contact.

Therefore, a configuration in which mechanical energy is applied to the metal body, while a relative movement in a normal, tangential, or combined direction thereof to the surfaces of the hard body and the metal body facing each other is performed, is preferred.

Second Embodiment (Apparatus for Producing a Hydrocarbon)

Next, an apparatus for producing a hydrocarbon according to a second embodiment of the present disclosure will be described in detail.

The apparatus for producing hydrocarbon from carbon dioxide according to the present disclosure includes a reaction vessel for applying mechanical energy to a metal body by solid-solid contact with a hard body, in the presence of a gas containing carbon dioxide and a hydrogen source. In addition, the apparatus also includes a gas introduction unit for introducing the gas containing carbon dioxide to the reaction vessel, a hydrogen source introduction unit for introducing the hydrogen source to the reaction vessel, and a gas discharge unit for discharging a gas containing a hydrocarbon produced in the reaction vessel. Using such an apparatus, hydrogen is added to carbon dioxide in the reaction vessel to produce a hydrocarbon.

The reaction vessel plays a role of proceeding with a decomposition/conversion reaction of carbon dioxide by applying mechanical energy to the metal body inside the vessel, and in the reaction vessel, contact or non-contact of the hard body with the metal body are repeated. Therefore, the hard body and the metal body perform movements such as vibration and rotation in the reaction vessel, and the hard body and the metal body may be configured to perform contact and non-contact movements repeatedly.

Alternatively, the entire reaction vessel performs movements such as vibration and rotation and energy is propagated to the hard body and the metal body inside, and as a result, the hard body and the metal body may be configured to perform contact and non-contact movements repeatedly.

The former is suitable for a configuration of an apparatus with easy handling of other units such as the gas introduction unit, the hydrogen source introduction unit, and the discharge unit. The latter is suitable for direct use of the mechanical energy in vibrating environments such as automobiles and airplanes.

It is preferred that in the gas introduction unit, the hydrogen source introduction unit, and the discharge unit, the on/off or amount of introduction and discharge can be controlled by an on-off valve.

FIGS. 1 to 6D are examples of configurations in which the metal body and the hard body are brought into contact.

FIG. 1 is an example in which a metal body 1 is put into a space made of a hard body 2, the metal body 1 inside also moves by giving vibration to every space, and the contact and non-contact with the hard body 2 are repeated to apply mechanical energy.

Figure 2A:
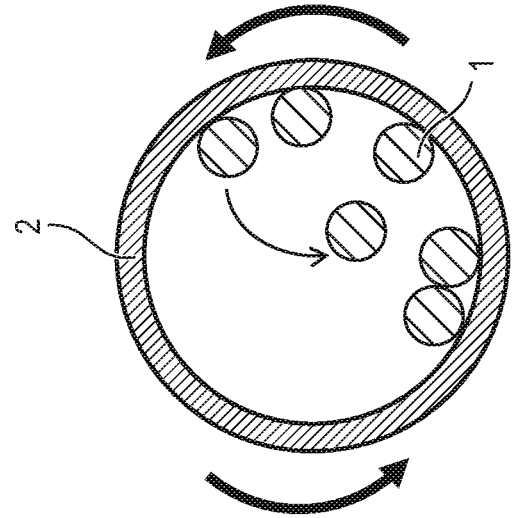
FIGS. 2A and 2B are examples of a configuration in which a metal body and a hard body are brought into a point contact, according to the present disclosure.
Figure 2B:
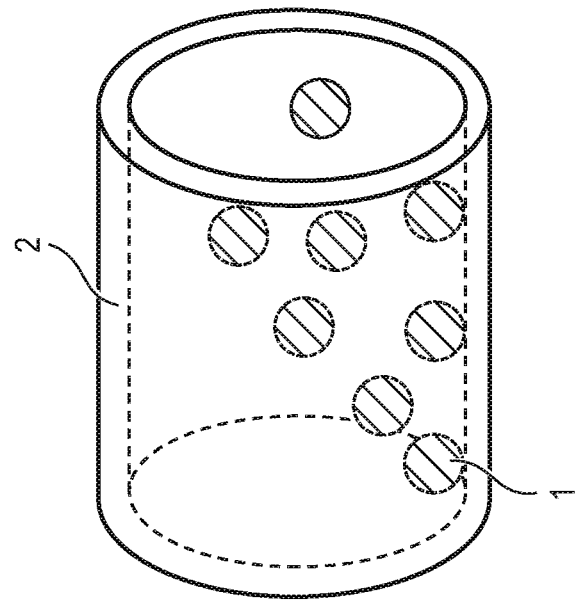

FIGS. 2A and 2B are examples of configurations in which by putting the metal body 1 into a cylindrical hard body 2 and rotating, the metal body 1 and the hard body 2 are brought into contact with each other. By rotating the hard body 2, the metal body 1 moves while contact and non-contact in a balance of a centrifugal force, a frictional force, and gravity are repeated. In particular, it is possible to give a strong impact when the metal body falls due to gravity.

In addition, in the configurations of FIGS. 1, 2A, and 2B, it is also possible for the hard body 2 to serve as the reaction vessel.

Figure 3A:
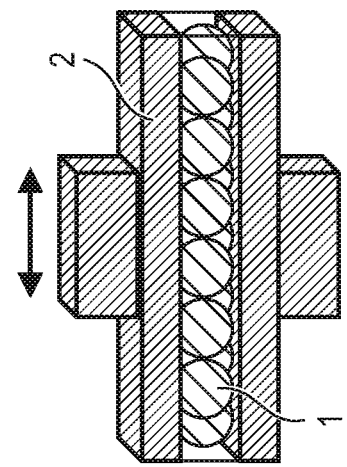
FIGS. 3A and 3B are examples of a configuration in which a metal body and a hard body are brought into a point contact, according to the present disclosure.
Figure 3B:
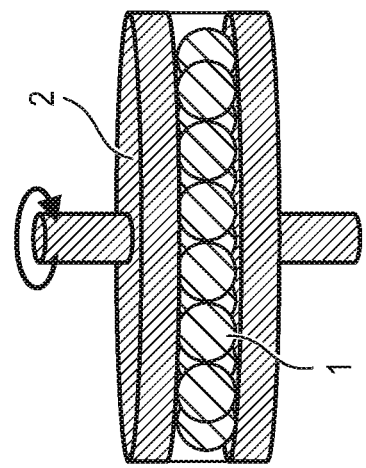

FIG. 3A is an example of a configuration in which by rotating the plate-like hard body 2 in contact with the metal body 1, the metal body 1 and the hard body 2 are brought into contact with each other. FIG. 3B is an example of a configuration in which by reciprocating the plate-shaped hard body 2 in the lateral direction in contact with the metal body 1, the metal body 1 and the hard body 2 are brought into contact with each other. In both cases, it is possible to apply mechanical energy to the metal body while repeating contact and non-contact.

Figure 4:
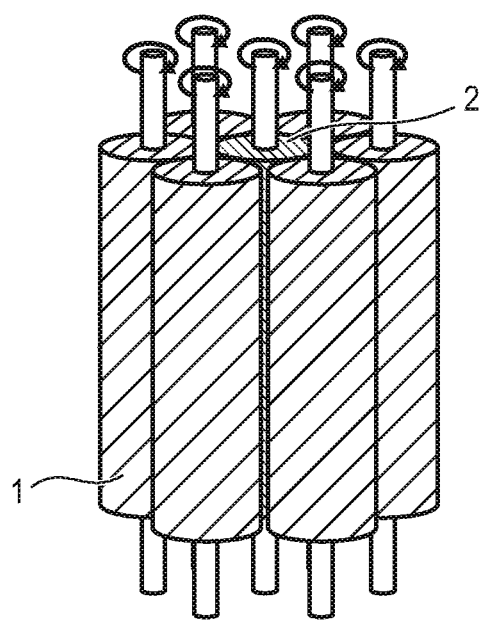
FIG. 4 is an example of a configuration in which a metal body and a hard body are brought into a line contact, according to the present disclosure.

FIG. 4 is an example of a configuration in which the metal body 1 and the hard body 2 are brought into a line contact. The hard body 2 and the metal body 1 have a cylindrical shape, and the hard body 2 and the surrounding metal body 1 rotate while being brought into contact with each other. By rotating the metal body 1, it becomes possible to repeat contact and non-contact.

Figure 5:
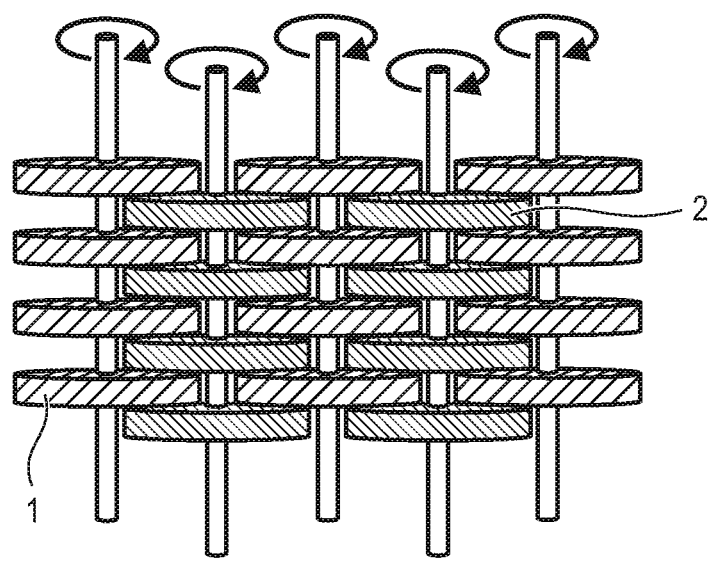
FIG. 5 is an example of a configuration in which a metal body and a hard body are brought into a surface contact, according to the present disclosure.

FIG. 5 is an example of a configuration in which the metal body 1 and the hard body 2 are brought into a surface contact. By taking a configuration in which the metal body 1 and the hard body 2 are disposed in an alternately staggered manner as illustrated in FIG. 5, it is possible to apply mechanical energy to the metal body 1 while repeating contact and non-contact. Use of a surface contact is preferred also from a viewpoint of increasing a contact area and improving reaction efficiency.

In configuration examples illustrated in FIGS. 6A, 6B, 6C, and 6D, a surface of the plate-shaped hard body 2 or metal body 1 is used, and an opposite surface of the metal body 1 or the hard body 2 has a fine projection structure. By rotating or moving such metal body 1 or hard body 2 in a tangential direction, mechanical energy is applied to the metal body 1 while the contact and non-contact of the metal body 1 and the hard body 2 are repeated.

Figure 6A:
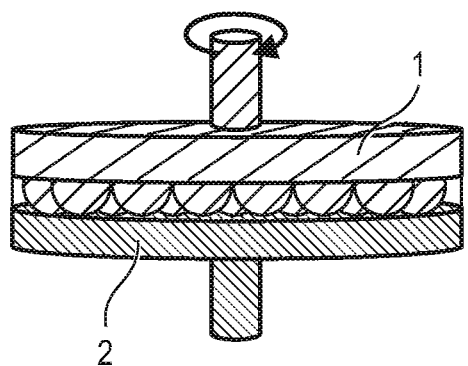
FIGS. 6A, 6B, 6C, and 6D are examples of a configuration in which a metal body and a hard body are brought into contact using a projection structure, according to the present disclosure.

FIG. 6A is an example of a configuration in which by rotating projection structure of the metal body 1 in contact with a plane of the hard body 2, the metal body 1 and the hard body 2 are brought into contact with each other.

Figure 6B:
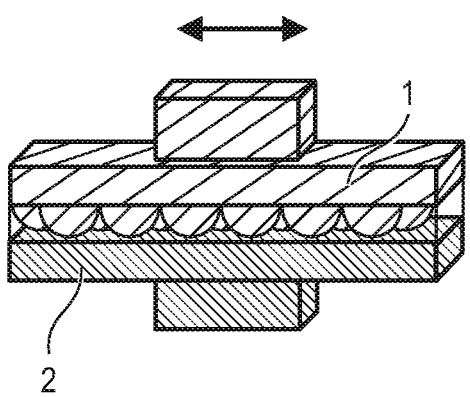
Figure 6C:
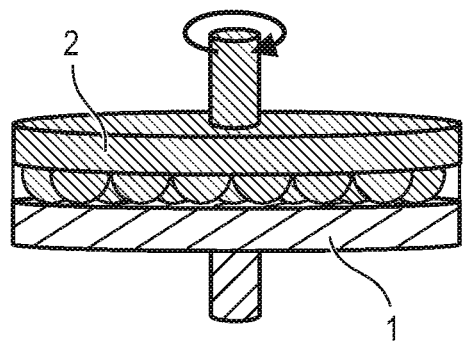

FIG. 6C is an example of a configuration in which by rotating projection structure of the hard body 2 in contact with a plane of the metal body 1, the metal body 1 and the hard body 2 are brought into contact with each other.

FIG. 6B is an example of a configuration in which by reciprocating projection structure of the metal body 1 in the lateral direction in contact with the hard body 2, the metal body 1 and the hard body 2 are brought into contact with each other.

Figure 6D:
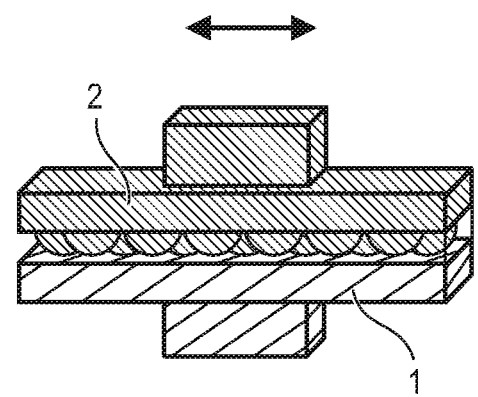

FIG. 6D is an example of a configuration in which by reciprocating projection structure of the hard body 2 in the lateral direction in contact with the metal body 1, the metal body 1 and the hard body 2 are brought into contact with each other.

In any of the configuration examples, it is possible to apply mechanical energy to the metal body 1 while the contact and non-contact of the metal body 1 and the hard body 2 are repeated.

It is possible to use any structure such as a depression, a groove structure, a mesh structure, and a lattice structure, as long as the contact and non-contact can be repeated by movement, without limitation to the fine projection structure.

Furthermore, in these configurations, the metal body 1 and the hard body 2 may be the same material. Furthermore, the metal body 1 and the hard body 2 may have different metal materials which induce a carbon dioxide reaction on the surface of the same material. In such case, since the surface of the hard body 2 is also involved in the reaction, it contributes to improved reaction efficiency.

Further, in the configurations of FIGS. 1, 2A, and 2B, it is possible to control an amount of the mechanical energy by the vibration speed and rotational speed of the hard body 2.

In the configurations of FIGS. 3A, 3B, 4, 5, 6A, 6B, 6C, and 6D, it is possible to control an amount of the mechanical energy by controlling the pressure, rotational speed, or moving speed of the hard body 2 to the metal body 1.

The metal body 1 and the hard body 2 are installed in the reaction vessel and constitute the entire reaction vessel.

In addition, the hard body 2 may be the metal body 1, and the inner wall surface of the reaction vessel itself may be the hard body 2 or the metal body 1.

The gas introduction unit included in the apparatus for producing a hydrocarbon according to the present disclosure may be connected to an exhaust pipe of a factory, a power plant, or the like. The gas introduction unit can be connected to the exhaust pipe to produce a hydrocarbon from a gas containing carbon dioxide discharged from the exhaust pipe.

It is preferred that the apparatus for producing a hydrocarbon further includes at least one of a metal body introduction unit for introducing the metal body and a metal body discharge unit for discharging the metal body.

Since the metal of the metal body is oxidized by the reaction, the ability to produce a hydrocarbon is reduced after the reaction. Therefore, when the hydrocarbon is produced continuously with high efficiency, it is preferred to provide a unit for introducing the metal body into the reaction vessel and a unit for discharging the metal body having reduced production ability.

Further, selection of introduction and discharge is facilitated by controlling the shape of the metal body. By repeating the contact and non-contact with the hard body, the metal body changes into a powder shape and is pulverized and peeled from the surface of the metal body as the reaction proceeds. Therefore, separation and discharge are easy by using a particle size separation mesh, a sedimentation phenomenon of a powder body, a weight difference, and the like.

In order to allow the separation, the size of the metal body before the reaction may be larger than that of the powder body after the reaction, and is preferably 1 mm or more.

Further, it is preferred that the reaction vessel or the gas discharge unit is provided with a detection unit for detecting the amount or concentration of carbon dioxide or the produced hydrocarbon.

Furthermore, it is preferred that a control unit for feeding back the detection results of the detection unit to control one or more of the amount of the gas containing carbon dioxide introduced to the reaction vessel and the amount of the mechanical energy is provided.

It is preferred that this control unit is a computer which operates a predetermined control program for controlling the entire apparatus for producing a hydrocarbon.

As described above, mechanical energy contributes to progress of the decomposition reaction of carbon dioxide and the hydrogen source, and changes the carbon dioxide consumption rate and the carbon dioxide decomposition rate. When the mechanical energy is insufficient, there is a possibility that the carbon dioxide consumption rate and the carbon dioxide decomposition rate are decreased. On the contrary, even in the case that the carbon dioxide consumption rate and the carbon dioxide decomposition rate are sufficient, when excessive mechanical energy is input, there is a possibility that energy efficiency is lowered.

When the detection unit for detecting the amount or concentration of carbon dioxide or the produced hydrocarbon is provided, it is possible to monitor the production efficiency of the apparatus in real time.

Furthermore, when one or more of the amount of the gas containing carbon dioxide introduced to the reaction vessel and the amount of the mechanical energy is controlled by the control unit through feed back of the detection results, apparatus performance can be maintained to be high.

It is preferred that the apparatus for producing a hydrocarbon is directly installed in equipment which discharges carbon dioxide, such as equipment which produces energy by burning so-called fossil fuels such as factories, power plants, automobiles, and airplanes, and combustion equipment for processing organic materials such as waste treatment plants.

Figure 9:
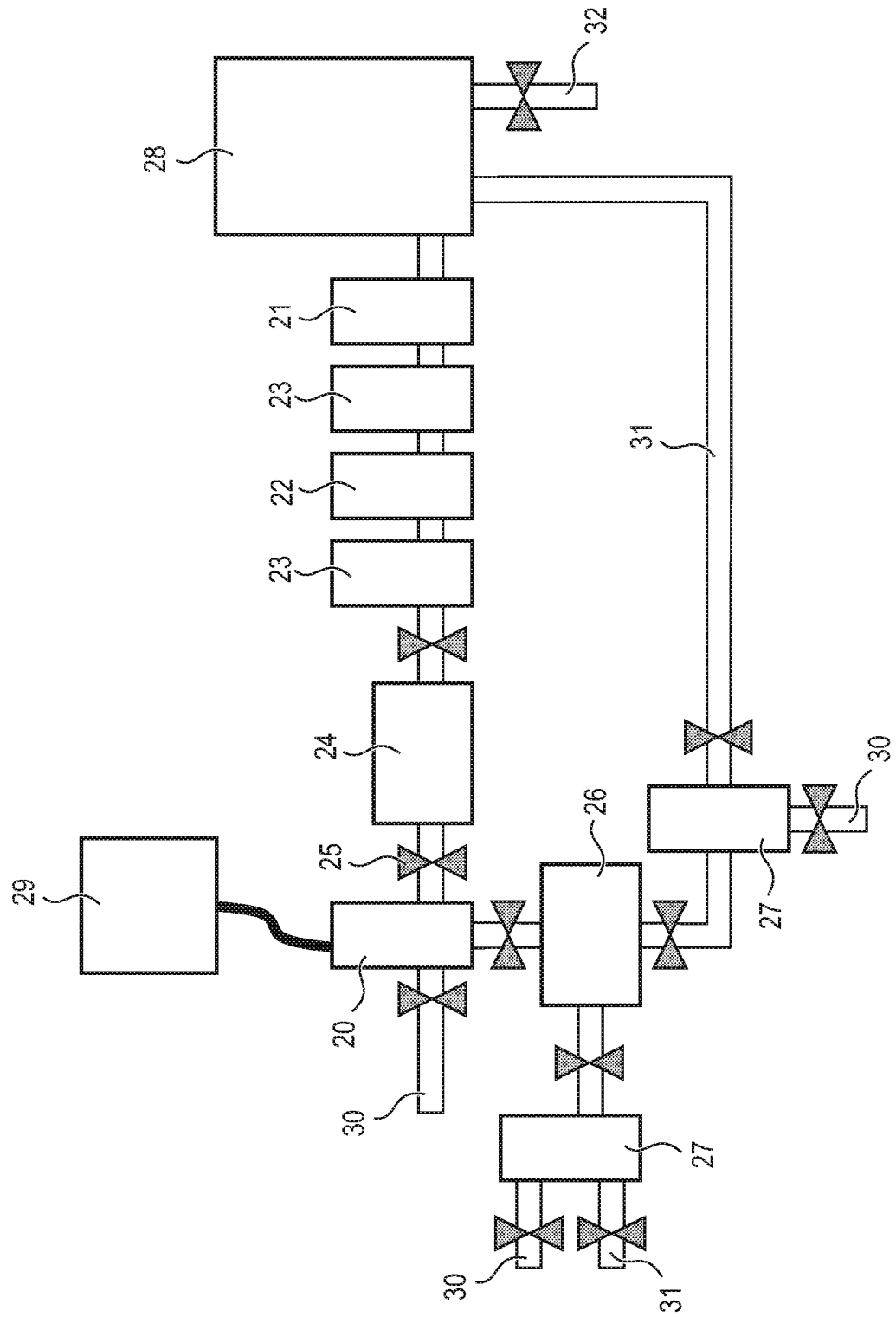
FIG. 9 is a schematic view illustrating an example of installing the apparatus for producing a hydrocarbon according to the present disclosure in carbon dioxide discharge equipment.

FIG. 9 is a schematic view illustrating an example in which an apparatus for producing a hydrocarbon 20 is installed in boiler equipment for a thermal power plant which burns fossil fuels, which is one type of the carbon dioxide discharge equipment.

In general, when a fuel supplied from a fuel supply unit 32 is burned by a boiler 28, sulfur oxides, nitrogen oxides, soot and dust, and the like are generated. Since these materials cause air pollution, for example, a flue gas denitration device 21, a flue gas desulfurization device 22, and a dust collector 23 illustrated in FIG. 9, and the like are often installed in the exhaust pipe.

It is preferred that the apparatus for producing a hydrocarbon 20 is installed via the exhaust pipe, likewise. Further, when a flue gas storage tank before production 24 and a valve 25 are installed in a front side of the apparatus for producing a hydrocarbon 20, it is possible to control an introduction speed, time, and the like of flue gas in the apparatus for producing a hydrocarbon 20.

When continuous processing is performed, the introduction speed of flue gas may be controlled depending on the processing capacity and the discharge capacity of the apparatus for producing a hydrocarbon 20. When batch processing is performed, the processing may be performed once in the closed apparatus for producing a hydrocarbon 20 by controlling the introduction amount from an introduction speed and time, and gas in the apparatus for producing a hydrocarbon 20 may be discharged out of the system after completion of a predetermined processing time.

Furthermore, a product storage tank 26 and a product separator 27 are installed in an outlet side of the apparatus for producing a hydrocarbon 20. Byproducts and the like separated from the product by the product separator 27 are discharged out of the system by a discharge unit 30.

The produced hydrocarbon is taken out to the outside, and may be reused as a mechanical energy source via a supply unit 31 for supplying the produced hydrocarbon to an apparatus driving part (not illustrated) for supplying drive energy to the apparatus for producing a hydrocarbon 20.

Alternatively, it is also preferred that the produced hydrocarbon is reused through the supply unit 31 for supplying the produced hydrocarbon to a combustion chamber (not illustrated) inside the boiler 28.

It becomes possible to appropriately compress and use the product obtained by separating a desired product from a plurality kinds of products or a mixed gas such as air, through the product separator 27. In addition, it is environmentally preferable that the drive energy of the apparatus for producing a hydrocarbon 20 is supplied from a renewable energy source 29.

Hereinafter, the present disclosure will be described in more detail using some experimental examples, but the present invention is not limited to these experimental examples and can be freely changed within the scope of obtaining the method of producing a hydrocarbon and the apparatus for producing a hydrocarbon having similar function and effects, such as materials, composition conditions, and reaction conditions.

EXAMPLE 1

Experimental Example 1

First, an example in which stainless steel is used as a hard body and a metal body, and mechanical energy is applied to the metal body by a ball milling method to produce a hydrocarbon from carbon dioxide is described.

The ball milling method is a method in which mechanical energy is applied to the inside by putting a ball into the vessel and moving the vessel by an external force, and is also suitable for this method.

A vessel having a volume of 80 mL and an inner wall made of SUS304 was charged with 100 balls made of SUS304 having a diameter of about 5 mm and 270 μL of water (15 mmol), and further filled with 1 atm of carbon dioxide and capped. In general, SUS304 is an alloy including Fe (ca. 69%), Ni (8 to 10%), and Cr (18 to 20%) as main components.

In addition, the operation of sucking in at 300 hPa for 6 seconds using a diaphragm pump and then filling with carbon dioxide from the balloon for preventing vaporization of water in the reaction vessel was repeated 6 times to perform gas replacement in the vessel. Theoretically, 99.9% or more of internal gas was replaced in the operation. An amount of carbon dioxide from a space inside the vessel was estimated to be about 3.1 mmol.

This vessel was set in ball mill equipment manufactured by Fritsch, Premium line-7 (PLP-7). The apparatus is planetary ball mill equipment and balls in the vessel are moved by rotating the vessel. When the balls collide with each other or the inner wall surface of the vessel, contact and non-contact are repeated, and mechanical energy can be applied.

Further, in the present experimental example, since stainless steel which is a hard metal is used for a vessel inner wall and a ball material, both can play a role of the hard body and the metal body.

After ball milling processing at the any rotation speed and processing time, gas in the vessel was collected and component analysis was performed by gas chromatography/thermal conductivity detector (GC/TCD). Table 1 shows reaction conditions, collected gas components, carbon dioxide consumption rates, and carbon dioxide decomposition rates. The carbon dioxide consumption rate is defined as a ratio of a value obtained by subtracting a remaining carbon dioxide amount from a charged carbon dioxide amount, relative to the charged carbon dioxide amount (Equation 1). Further, the carbon dioxide decomposition rate is defined as a ratio of a produced amount of methane gas, relative to a charged carbon dioxide amount (Equation 2).

$$\text{Carbon dioxide consumption rate (\%)} = (CO_2 \text{ charge amount} - CO_2 \text{ recovery amount})/CO_2 \text{ charge amount} \times 100 \quad \text{(Equation 1)}$$

$$\text{Carbon dioxide decomposition rate (\%)} = CH_4 \text{ charge amount}/CO_2 \text{ charge amount} \times 100 \quad \text{(Equation 2)}$$

In addition, the case in which the carbon dioxide decomposition rate is more than 100% is due to a measurement error or an incorporation of some impurities, and does not impair the effect of the present disclosure.

TABLE 1

| Reaction conditions | | Collected gas components | | | | Reaction efficiency | |
|---|---|---|---|---|---|---|---|
| Rotation speeds (rpm) | Processing time (min) | $H_2$ (mmol) | $CH_4$ (mmol) | $C_2H_6$ (mmol) | $CO_2$ (mmol) | $CO_2$ consumption rate (%) | $CO_2$ decomposition rate (%) |
| 800 | 90 | 13.2 | 0.652 | 0.0435 | 0 | 100 | 21.0 |
| 800 | 180 | 10.4 | 1.86 | 0.0672 | 0 | 100 | 60.1 |
| 1100 | 90 | 9.26 | 3.29 | 0.0513 | 0 | 100 | 106.1 |

As a result of analysis, a decrease in a carbon dioxide amount and production of hydrogen and hydrocarbon were confirmed, and thus, it was confirmed that hydrocarbons in which hydrogen is added to carbon dioxide, that is, a hydrocarbon was produced by this method. Further, it was confirmed that the carbon dioxide decomposition rate into methane gas was also a high value of almost 100%, and this method is a highly efficient method.

Experimental Example 2

This experimental example is an example in which stainless steel is used as a hard body and a metal body, water is used as a hydrogen source, and mechanical energy is applied to the metal body by a ball milling method to produce a hydrocarbon from carbon dioxide, as in Experimental Example 1. However, isotope heavy water ($D_2O$) was used instead of water and isotope $^{13}CO_2$ was used instead of carbon dioxide ($^{12}CO_2$).

After ball milling processing as in Experimental Example 1, gas in the vessel was collected and component analysis was performed by GC/TCD. In addition, measurement was performed also by gas chromatography/mass spectrometer (GC/MS) in addition to GC/TCD, for performing isotope analysis.

As a result of using $^{13}CO_2$, after ball milling processing as in Experimental Example 1, it was found by GC/TCD analysis that a peak of carbon dioxide almost disappeared and a peak of hydrocarbons was detected. Furthermore, as a result of mass analysis by GC/MS, a peak with a high molecular weight was detected depending on the number of carbons. These show the production of hydrocarbons composed of $^{13}C$, and it was confirmed that a hydrocarbon was produced from the charged carbon dioxide.

Further, when heavy water was used instead of water also, it was found that a peak of carbon dioxide almost disappeared and a peak of hydrocarbons was detected, after the ball milling processing.

Furthermore, when mass analysis was performed by GC/MS, a peak having a high molecular weight was present, and it was found that the produced hydrocarbons contain deuterium. Therefore, it was confirmed that the introduced water was the hydrogen source for this reaction, hydrogen was produced by decomposition of the water, and the hydrogen was added to carbon dioxide to produce hydrocarbons.

Experimental Example 3

This experimental example is an example in which stainless steel is used as a hard body and a metal body, water is used as a hydrogen source, and mechanical energy is applied to the metal body by a ball milling method to produce a hydrocarbon from carbon dioxide, as in Experimental Example 1. A chemical state of the metal body was analyzed for each reaction time, and an intermediate state was specified.

After ball milling processing at the rotation speed of 1100 rpm for an optional processing time, gas in the vessel was recovered and component analysis was performed by GC/TCD. Table 2 shows reaction conditions, collected gas components, carbon dioxide consumption rates, and carbon dioxide decomposition rates.

TABLE 2

| Reaction conditions | | Collected gas components | | | | Reaction efficiency | |
|---|---|---|---|---|---|---|---|
| Rotation speed (rpm) | Processing time (min) | $H_2$ (mmol) | $CH_4$ (mmol) | $C_2H_6$ (mmol) | $CO_2$ (mmol) | $CO_2$ consumption rate (%) | $CO_2$ decomposition rate (%) |
| 1100 | 15 | 9.32 | 0.143 | 0.0083 | 0.996 | 67.9 | 4.6 |
| 1100 | 30 | 11.7 | 0.708 | 0.0227 | 0.643 | 79.3 | 22.8 |
| 1100 | 60 | 8.89 | 2.72 | 0.0519 | 0 | 100 | 87.9 |
| 1100 | 90 | 9.26 | 3.29 | 0.0513 | 0 | 100 | 106.1 |

It was confirmed that with an increase in reaction time, the carbon dioxide consumption rate and the carbon dioxide decomposition rate were increased, but when the reaction time was short, the carbon dioxide consumption rate and the carbon dioxide decomposition rate did not match.

Metal balls subjected to ball milling processing were changed from a glossy color to a black color, and the presence of black powder which was considered to be pulverized and peeled off from the surface, was confirmed. The black component or a ball surface changed to a black color was analyzed by X-ray photoelectron spectroscopy (XPS).

As a result, it was confirmed that a peak of the metal (Fe, Cr, or Ni) was shifted from a position before processing and the metal was oxidized. Furthermore, as a result of analyzing a peak of C1s and a peak of O1s, a peak attributed to a carbonate was observed in a sample after being subjected to ball milling processing under a short reaction time condition, in particular, 15 minutes. The peak attributed to a carbonate was decreased with increasing reaction time.

That is, by these chemical measurements and analyses, this reaction step in which carbon dioxide is metal carbonated on the surface of the metal body, and hydrogen is added to the carbonate by further applying mechanical energy in the presence of hydrogen, thereby proceeding with addition of hydrogen to carbon dioxide, was confirmed.

Experimental Example 4

This experimental example is an example in which stainless steel is used as a hard body and a metal body, water is used as a hydrogen source, and mechanical energy is applied to the metal body by a ball milling method to produce a hydrocarbon from carbon dioxide, as in Experimental Example 1. Particularly, this is an example in which the amount of mechanical energy is controlled by the reaction conditions (rotation speed and processing time), and the carbon dioxide consumption rate and the carbon dioxide decomposition rate are controlled.

After ball milling processing at an arbitrary rotation speed and processing time, the gas in the vessel was collected and component analysis was performed by GC/TCD, as in Example 1. Table 3 shows reaction conditions, carbon dioxide consumption rates, and carbon dioxide decomposition rates.

TABLE 3

| Reaction conditions | | Reaction efficiency | |
|---|---|---|---|
| Rotation speed (rpm) | Processing time (min) | $CO_2$ consumption rate (%) | $CO_2$ decomposition rate (%) |
| 200 | 90 | 8.5 | 0 |
| 600 | 180 | 97.7 | 1.4 |
| 800 | 60 | 74.5 | 10.8 |
| 800 | 90 | 100 | 21.0 |
| 800 | 180 | 100 | 60.1 |
| 1100 | 90 | 100 | 106.1 |

It was found that the carbon dioxide consumption rate and the carbon dioxide decomposition rate were different, depending on the rotation speed and the processing time. In particular, the effect of the rotation speed was large and almost no decomposition occurred at 600 rpm or less.

As a result of performing XPS analysis on black powder which was considered to be pulverized and peeled off from a metal ball surface after processing at 600 rpm for 180 minutes, a clear peak attributed to a carbonate was confirmed, as in Example 3. Therefore, it was confirmed that carbon dioxide was carbonated but did not reach decomposition (hydrocarbonation), under this conditions.

Further, the carbon dioxide consumption rate was also low at the low rotation speed of 200 rpm. The rotation speed control at the time of ball milling is synonymous with controlling the centrifugal force and acceleration applied to the ball in the container, that is, the metal body. And it is nothing other than controlling the collision force, stress and friction force between the metal body and the hard body, that is, the amount of mechanical energy applied per unit area of the metal body.

By controlling the mechanical energy as in this experimental example, it is possible to control a production amount of a hydrocarbon (hydrocarbons) to be produced.

Experimental Example 5

This experimental example is an example in which stainless steel is used as a hard body and a metal body, water is used as a hydrogen source, and mechanical energy is applied to the metal body by a ball milling method to produce a hydrocarbon from carbon dioxide, as in Experimental Example 1. Particularly, this is an example in which by reaction conditions (amount of the metal body), an amount of the mechanical energy is controlled, and the carbon dioxide consumption rate and the carbon dioxide decomposition rate are controlled.

After ball milling processing for 90 minutes at the arbitrary rotation speed with the number of input balls made of SUS304 being changed, gas in the vessel was collected and component analysis was performed by GC/TCD, as in Example 1. Table 4 shows reaction conditions, carbon dioxide consumption rates, and carbon dioxide decomposition rates.

TABLE 4

| Reaction conditions | | | | Reaction efficiency | |
|---|---|---|---|---|---|
| | | | | $CO_2$ | $CO_2$ |
| Rotation speed (rpm) | Processing time (min) | Number of balls (number) | Amount of added water (mmol) | consumption rate (%) | decomposition rate (%) |
| 800 | 90 | 100 | 15 | 100 | 21.0 |
| 800 | 90 | 200 | 12.5 | 100 | 79.7 |
| 800 | 90 | 200 | 15 | 100 | 71.6 |
| 800 | 90 | 250 | 12.5 | 100 | 94.4 |
| 600 | 90 | 250 | 12.5 | 87.4 | 1.5 |

It was found that the carbon dioxide decomposition rate was increased by increasing the number of balls. This is a result of an increase in the reaction rate because the surface area of the metal body to which mechanical energy is applied, that is, the contact area with the hard body is increased. As such, the carbon dioxide decomposition rate can be improved by increasing a total amount of mechanical energy applied to the metal body in the reaction vessel per unit time.

In addition, as shown in Experimental Example 4 in which a large carbon dioxide decomposition rate was not seen under a 600 rpm condition, it was considered that this is because the amount of the mechanical energy applied per unit area of the metal body was insufficient. It is also the feature of the present disclosure that the carbon dioxide consumption rate and the carbon dioxide decomposition rate are controllable by controlling the entire apparatus, based on such experimental results.

zirconium oxide having a diameter of 5 mm and water, and powder of an elemental metal was further added, and carbon dioxide was filled in the vessel to perform ball milling processing.

Since zirconium oxide which is a material of the inner wall of the vessel and the ball is already an oxidant and is a high-valence material, zirconium oxide has low reactivity. Therefore, zirconium oxide plays only the role as the hard body and the added metal powder plays the role of metal body.

After ball milling processing at the rotation speed of 1100 rpm for a processing time of 90 minutes, gas in the vessel was collected and component analysis was performed by GC/TCD. Table 5 shows reaction conditions, collected gas components, carbon dioxide consumption rates, and carbon dioxide decomposition rates.

TABLE 5

| | Reaction conditions | | Collected gas components | | | | | Reaction efficiency | |
|---|---|---|---|---|---|---|---|---|---|
| Metal | Rotation speed (rpm) | Processing time (min) | $H_2$ (mmol) | $CH_4$ (mmol) | $C_2H_6$ (mmol) | $CO_2$ (mmol) | CO | $CO_2$ consumption rate (%) | $CO_2$ decomposition rate (%) |
| Fe | 1100 | 90 | 0.688 | 0.379 | 0.0015 | 0.0217 | (+) | 98.1 | 32.6 |
| Cr | 1100 | 90 | 0.552 | 0.0616 | 0 | 0.299 | (+) | 74.2 | 5.3 |
| Ni | 1100 | 90 | 0.586 | 0.150 | 0.002 | 0.477 | (+) | 58.8 | 12.9 |

Figure 10:
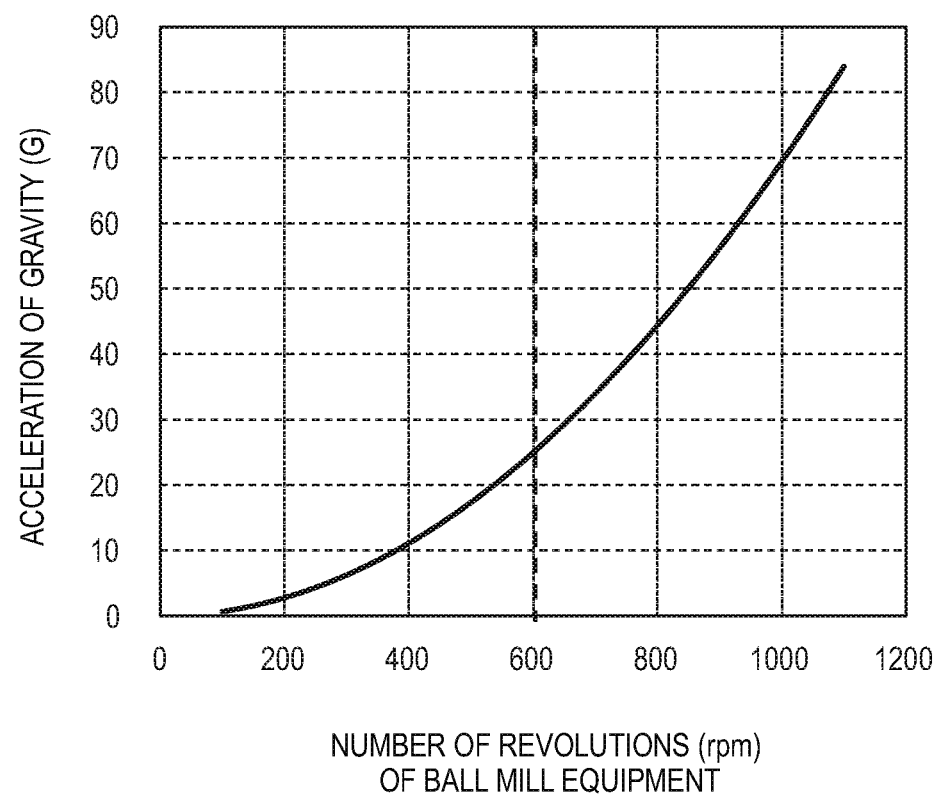
FIG. 10 is a graph indicating a relationship between the rotation speed of ball mill equipment and a gravitational acceleration G applied to a ball.

It is known that in the ball mill equipment, contact and friction between the ball and the vessel inner wall due to a centrifugal force are more dominant than collision between balls, generally at 500 to 600 rpm or more. The gravitational acceleration G applied to the ball in the ball mill equipment by a centrifugal force is defined by a revolution radius, a vessel radius, a ratio of rotation to revolution, and the rotation speed. FIG. 10 illustrates the results of calculating the relationship between the gravitational acceleration G and the rotation speed.

In both Experimental Examples 4 and 5, almost no decomposition of carbon dioxide occurred at 600 rpm or less, and thus, it was considered that the gravitational acceleration of about 30 G or more is needed for proceeding with the present reaction efficiently. Furthermore, the contact pressure per unit area at this time was estimated to be 30 kPa from the mass of the SUS304 ball having a diameter of about 5 mm and a contact area (about 5 mm²). Therefore, in order to perform the present disclosure more efficiently, it is preferred to apply mechanical energy to the metal body so that the contact pressure per unit area of the metal body is 30 kPa or more.

Experimental Example 6

This experimental example is an example in which zirconium oxide which is a metal oxide having low reactivity was used as the hard body, various metal powders were used as the metal body, and mechanical energy was applied to the metal body by a ball milling method to produce hydrocarbons from carbon dioxide. The reactivity of an alloy was compared with that of an elemental metal.

A vessel having a volume of 80 ml and an inner wall made of zirconium oxide was charged with 100 balls made of Even in the case of using metal powder of iron, chromium, or nickel, the consumption and decomposition (production of hydrocarbons) of carbon dioxide were confirmed. However, it was confirmed that it is preferred to use the metal ball made of SUS described above as the metal body from a viewpoint of reaction efficiency, and the alloy is more preferred.

Example 2

The present example is an example of an apparatus for producing a hydrocarbon.

Figure 7:
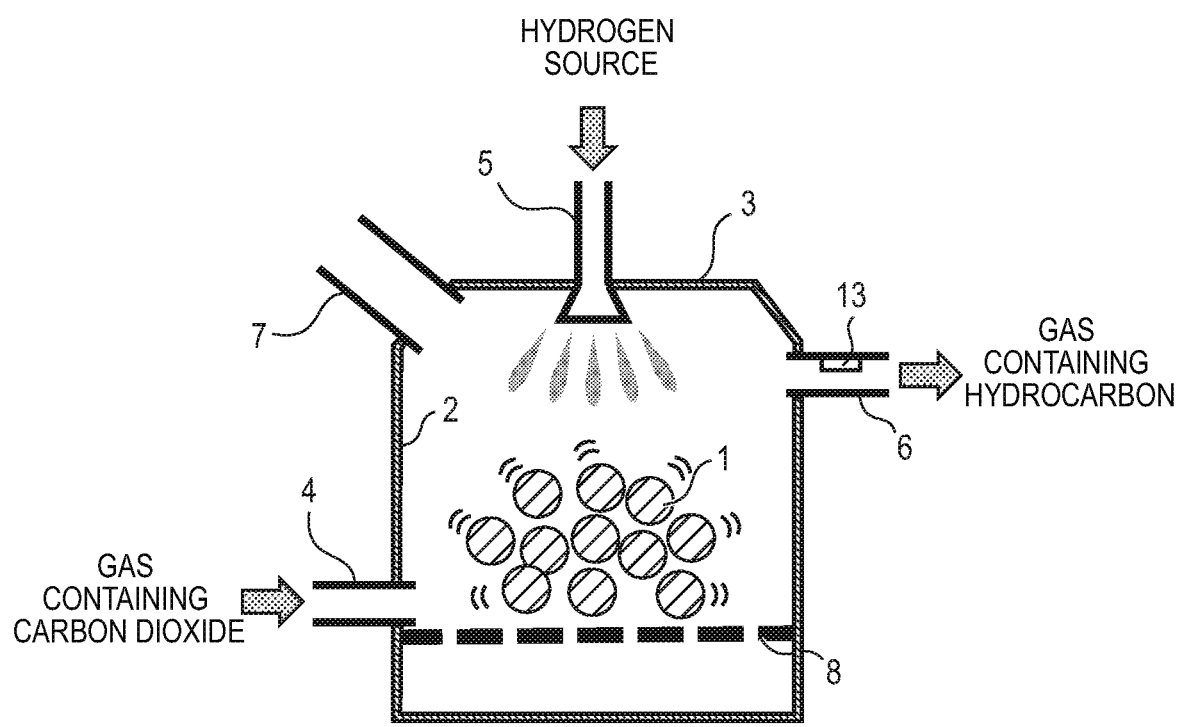
FIG. 7 is a schematic view illustrating an example of an apparatus for producing a hydrocarbon according to the present disclosure.

FIG. 7 is a schematic view illustrating an apparatus for producing a hydrocarbon in the present example. In the apparatus for producing a hydrocarbon illustrated in FIG. 7, the metal body 1 was introduced from the metal body introduction unit 7 to the reaction vessel 3, and a hard metal was adopted in the inner wall of the reaction vessel to obtain the hard body 2.

The reaction vessel 3 was further provided with a gas introduction unit 4, a hydrogen source introduction unit 5, and a gas discharge unit 6, and was configured so that on/off or an amount of introduction and discharge were controllable by an on-off valve which is not illustrated. When a hydrocarbon which is lighter than carbon dioxide, such as methane gas and ethane gas is produced, it is preferred to install the gas discharge unit 6 above the gas introduction unit 4, as shown in the present example. Further, when gas which is heavier than carbon dioxide is produced, the gas discharge unit 6 may be installed below the gas introduction unit 4. A plurality of gas discharge units 6 may be installed for sorting by weight.

In the apparatus for producing a hydrocarbon according to the present example, the gas discharge unit 6 is provided with a detection unit 13 for detecting the amount or concentration of carbon dioxide or the produced hydrocarbon.

In the present example, by vibrating the entire reaction vessel 3, the metal body 1 inside can also move, and the contact and non-contact with the hard body 2 can be repeated to apply mechanical energy. The reaction vessel is vibrated by rotation and vertical and horizontal movements, and it is possible to control the amount of the mechanical energy by the speed, the amplitude, and the like.

It is preferred that a control unit (not illustrated) for controlling such on-off valve, the gas introduction unit 4, the hydrogen source introduction unit 5, and the gas discharge unit 6, and controlling the vibration strength and time of the reaction vessel 3, is provided.

It is preferred that this control unit is a computer which operates a predetermined control program for controlling the entire apparatus for producing a hydrocarbon.

In addition, a driving source of the vibration motion may be electric energy, and various types of renewable energy are currently converted into electric power and preferably used from a viewpoint of diversity. Further, when an automobile, an airplane, or the like is used in an apparatus having vibration itself, it is preferred to convert the vibration as it is to vibration energy of the present apparatus and use the energy from a viewpoint of energy efficiency.

Further, it is preferred that a sensor was installed as a detection unit 13 relating to temperature, pressure, and gas components in the reaction vessel 3, and the introduction amount and discharge amount of gas, and the introduction amount of the hydrogen source are controlled for securing safety, controlling a reverse reaction, controlling the concentration of a hydrocarbon to be produced, and the like.

Furthermore, it is preferred to install a measuring device (not illustrated) relating to the amount of the remaining metal body in the reaction vessel 3, and to control the introduction amount of the metal body from an appropriate metal body introduction unit for maintaining high reaction efficiency.

The amount of the introduction gas, discharge gas, the hydrogen source, and the metal body are controlled by executing the control unit described above.

In the apparatus for producing a hydrocarbon according to the present example, a metal body discharge unit 8 having a mesh structure is installed below the metal body 1. The oxidized, pulverized and peeled metal body is discharged out of the system.

It is possible to produce a hydrocarbon from carbon dioxide with high efficiency, by using the apparatus for producing a hydrocarbon according to the example.

Example 3

The present example is another example of the apparatus for producing a hydrocarbon.

Figure 8:
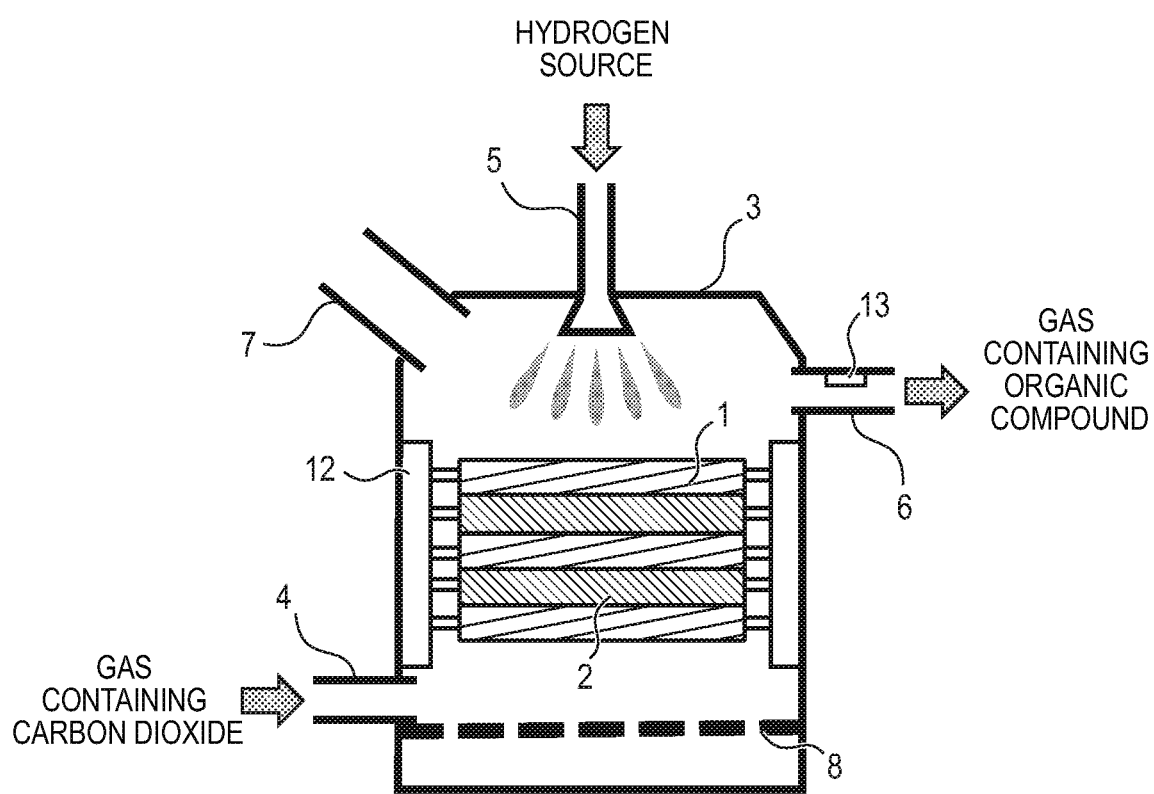
FIG. 8 is a schematic view illustrating an example of the apparatus for producing a hydrocarbon according to the present disclosure.

FIG. 8 is a schematic view illustrating the apparatus for producing a hydrocarbon in the present example. In the apparatus for producing a hydrocarbon illustrated in FIG. 8, the cylindrical metal body 1 and hard body 2 were introduced to the reaction vessel 3. The metal body 1 and the hard body 2 are rotated while being maintained in a positional relationship for maintaining a contact state by a drive unit 12.

The reaction vessel 3 was further provided with the gas introduction unit 4, the hydrogen source introduction unit 5, and the gas discharge unit 6.

Further, in the apparatus for producing a hydrocarbon according to the present example, the gas discharge unit 6 is provided with a detection unit 13 for detecting the amount or concentration of carbon dioxide or the produced hydrocarbon.

In the present example, it is possible to supply the mechanical energy by rotating the metal body 1 and the hard body 2 in the reaction vessel 3 and repeating the contact and non-contact of the metal body 1 and the hard body 2. It is also possible to control the amount of the mechanical energy by controlling the rotational speed and the contact pressure.

In addition, a driving source of the rotational movement may be electric energy, and various renewable energies are currently converted into electric power and are preferably used from a viewpoint of diversity. In addition, when the power source itself is kinetic energy, like hydroelectric power generation, wind power generation, and the like, it is preferred to convert the kinetic energy into rotational energy directly and use the rotational energy from a viewpoint of energy efficiency.

Further, a sensor may be installed in the reaction vessel as the detection unit 13 relating to temperature, pressure, and gas components. Furthermore, it is preferred to install a measuring device relating to the amount of the remaining metal body inside the reaction vessel 3. It is possible to measure the amount of the remaining metal body by measuring a change in the weight or the diameter of the cylindrical metal body.

Furthermore, in the apparatus for producing a hydrocarbon according to the present example, the metal body discharge unit 8 is installed.

It is preferred that a control unit (not illustrated) for controlling the gas introduction unit 4, the hydrogen source introduction unit 5, and the gas discharge unit 6, and controlling the driving amount and the drive time of the driving unit 12 as in the present example, is provided.

It is preferred that this control unit is a computer which operates a predetermined control program for controlling the entire apparatus for producing a hydrocarbon.

It is possible to produce a hydrocarbon from carbon dioxide with high efficiency, by using the apparatus for producing a hydrocarbon according to the example.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2018-197182, filed Oct. 19, 2018, which is hereby incorporated by reference herein in its entirety.

What is claimed is:

1. An apparatus comprising:
a vessel for providing a space;
a first introduction unit for introducing a gas containing carbon dioxide to the space,
a second introduction unit for introducing a hydrogen source to the space; and
a discharge unit for discharging a gas containing hydrocarbon from the space,
wherein the vessel is configured so that mechanical energy is applied to a metal body in the space by a contact between the metal body and a hard body with a contact pressure per unit area of the metal body being 30 kPa or more.

2. The apparatus according to claim 1, further comprising unit for introducing the metal body to the space and/or discharging the metal body from the space.

3. The apparatus according to claim 1, further comprising a detection unit for detecting an amount or concentration of carbon dioxide or hydrocarbon in the space.

4. The apparatus according to claim 3, further comprising a control unit for controlling, on a basis of a detection result of the detection unit, an amount of carbon dioxide in the space and/or an amount of the mechanical energy.

5. The apparatus according to claim 1, further comprising a supply unit for supplying the mechanical energy to be applied to the metal body using the hydrocarbon.

6. The apparatus according to claim 1, wherein the mechanical energy is generated by a ball milling method.

7. The apparatus according to claim 1, wherein the metal body is a ball.

8. The apparatus according to claim 1, wherein the metal body is made of alloy.

9. The apparatus according to claim 1, wherein the metal body is made of stainless steel.

10. The apparatus according to claim 1, wherein the metal body and the hard body are made of the same material.

11. An equipment comprising:
the apparatus according to claim 1; and
a renewable energy source for supplying drive energy of the apparatus.

12. An equipment comprising:
the apparatus according to claim 1; and
a supply unit for supplying a fuel which is burned to discharge the carbon dioxide introduced by the first introduction unit.

13. An equipment comprising:
the apparatus according to claim 1; and
a separator for separating a first product and a second product in the gas discharged by the discharge unit.

14. A method of producing gas, comprising:
providing the apparatus according to claim 1;
introducing a gas containing carbon dioxide to the space by the first introduction unit;
introducing a hydrogen source to the space by the second introduction unit;
repeating a contact and a non-contact between the metal body and the hard body; and
discharging a gas containing hydrocarbon from the space by the discharge unit.

15. The method according to claim 14, wherein the hydrogen source is water.

16. The method according to claim 14, wherein the hydrocarbon is produced in the space.

17. The method according to claim 14, wherein the hydrocarbon includes carbon derived from the carbon dioxide and hydrogen derived from the hydrogen source.

18. The method according to claim 14, wherein in the space, metal carbonate is generated by a reaction between the carbon dioxide and the metal body.

19. The method according to claim 18, wherein in the space, the hydrocarbon is produced by a reaction between the metal carbonate and hydrogen.

20. The method according to claim 19, wherein in the space, the hydrogen is extracted from the hydrogen source by a reduction of the hydrogen source.

21. The method according to claim 15, wherein the gas discharged by the discharge unit contains methane.

22. The method according to claim 14, wherein the gas discharged by the discharge unit contains ethane and/or propane.

23. The method according to claim 14, wherein the carbon dioxide is consumed and/or decomposed in the space.

* * * * *